United States Patent
Gan et al.

(10) Patent No.: US 10,251,833 B2
(45) Date of Patent: Apr. 9, 2019

(54) PORE MINIMIZER

(71) Applicant: Mary Kay Inc., Addison, TX (US)

(72) Inventors: David Gan, Southlake, TX (US);
Geetha Kalahasti, Addison, TX (US);
Lisha Van Pelt, Addison, TX (US)

(73) Assignee: Mary Kay Inc., Addison, TX (US)

( * ) Notice: Subject to any disclaimer, the term of this patent is extended or adjusted under 35 U.S.C. 154(b) by 535 days.

(21) Appl. No.: 14/794,489

(22) Filed: Jul. 8, 2015

(65) Prior Publication Data
US 2016/0008268 A1 Jan. 14, 2016

Related U.S. Application Data

(60) Provisional application No. 62/023,387, filed on Jul. 11, 2014.

(51) Int. Cl.
| A61K 36/00 | (2006.01) |
| A61K 36/48 | (2006.01) |
| A61K 8/98 | (2006.01) |
| A61K 8/34 | (2006.01) |
| A61K 8/37 | (2006.01) |
| A61K 8/44 | (2006.01) |
| A61K 8/58 | (2006.01) |
| A61K 8/81 | (2006.01) |
| A61K 8/891 | (2006.01) |
| A61K 8/894 | (2006.01) |
| A61K 8/97 | (2017.01) |
| A61Q 19/00 | (2006.01) |

(52) U.S. Cl.
CPC .............. *A61K 8/987* (2013.01); *A61K 8/345* (2013.01); *A61K 8/37* (2013.01); *A61K 8/44* (2013.01); *A61K 8/585* (2013.01); *A61K 8/8152* (2013.01); *A61K 8/891* (2013.01); *A61K 8/894* (2013.01); *A61K 8/97* (2013.01); *A61Q 19/00* (2013.01); *A61Q 19/008* (2013.01); *A61Q 19/005* (2013.01)

(58) Field of Classification Search
None
See application file for complete search history.

(56) References Cited

U.S. PATENT DOCUMENTS

| 6,217,913 | B1 | 4/2001 | Mohammadi | 424/520 |
| 6,432,389 | B1 * | 8/2002 | Hansenne | A61K 8/37 424/400 |
| 6,680,062 | B2 | 1/2004 | Muizzuddin et al. | 424/401 |
| 6,787,571 | B2 | 9/2004 | Jacobs et al. | 514/681 |
| 7,758,878 | B2 | 7/2010 | Scimeca et al. | 424/401 |
| 8,535,738 | B2 | 9/2013 | Collins et al. | 424/750 |
| 8,551,462 | B2 * | 10/2013 | Goldstein | A61K 8/35 424/70.1 |
| 2005/0048008 | A1 | 3/2005 | Gupta | 424/59 |
| 2009/0226386 | A1 * | 9/2009 | Brillouet | A61K 8/732 424/59 |
| 2010/0125048 | A1 | 5/2010 | Lee et al. | 514/18.8 |
| 2010/0189669 | A1 | 7/2010 | Hakozaki | 514/1.1 |
| 2010/0221245 | A1 * | 9/2010 | Kunin | A61K 8/38 424/133.1 |
| 2011/0020414 | A1 | 1/2011 | Kunin | 424/401 |
| 2011/0236499 | A1 | 9/2011 | Billis | 424/520 |
| 2012/0237540 | A1 | 9/2012 | Florence et al. | |
| 2013/0118517 | A1 * | 5/2013 | Foley | A61K 8/042 132/200 |
| 2013/0177512 | A1 * | 7/2013 | Kurfurst | A61K 8/606 424/59 |
| 2013/0243710 | A1 * | 9/2013 | Koganov | A61K 8/97 424/62 |
| 2013/0315846 | A1 * | 11/2013 | Collier | A61K 8/97 424/59 |

FOREIGN PATENT DOCUMENTS

| CN | 102284052 | | 12/2011 |
| CN | 103301054 | * | 9/2013 |
| FR | 2989270 A1 | * | 10/2013 |
| JP | 2009242296 A | * | 10/2009 |
| KR | 10-2010-0090530 | | 8/2010 |
| KR | 10-1081424 | | 11/2011 |
| WO | WO 2012/149110 | | 11/2012 |
| WO | WO 2013/046137 | | 4/2013 |
| WO | WO 2013/149323 | | 10/2013 |

OTHER PUBLICATIONS

International Search Report and Written Opinion issued in PCT/US2015/039513, dated Sep. 24, 2015.
Extended European Search Report issued in European Application No. 15819510.7, dated Dec. 11, 2017.

* cited by examiner

*Primary Examiner* — Christopher R Tate
(74) *Attorney, Agent, or Firm* — Norton Rose Fulbright US LLP

(57) ABSTRACT

Described herein are compositions that contract and reduce pore size. The compositions of the disclosure are also useful for collagen contraction of the skin, calming skin, and reducing oil on the skin. The compositions comprise cosmetic ingredients such as glycerin; cyclopentasiloxane; polysilicone-11; pentaerythrityl tetraethylhexanoate; dipropylene glycol; methyl methacrylate crosspolymer; betaine; bis-PEG/PPG-16/PPG-16/16 PEG/16 dimethicone; *Albizia julibrissin* bark extract; *Evodia rutaecarpa* fruit extract; hydrolyzed soy flour; sea whip extract; and a dermatologically acceptable vehicle.

14 Claims, No Drawings

PORE MINIMIZER

CROSS REFERENCE TO RELATED APPLICATIONS

This application claims the benefit of U.S. Provisional Application No. 62/023,387 filed Jul. 11, 2014, the contents of which are incorporated into the present application by reference.

BACKGROUND OF THE INVENTION

A. Field of the Invention

The present invention generally relates to methods and compositions useful for minimizing pore size or the appearance thereof.

B. Description of Related Art

Mammalian skin is characterized by thousands of pores which function as openings for sebaceous (oil-producing) and sudoriferous (sweat-producing) glands and hair follicles. Pores generally serve as openings for the secretion of glandular products such as sebum, and orifices for externally applied substances, including lotions, creams, and cosmetics. Skin pores are large and numerous on the face and scalp, areas of maximum exposure. For facial areas, the density ranges from 400 to 800 pores/cm$^2$, compared with about 50 pores/cm$^2$ on the arms and legs. The forehead, nose, and nasolabial folds are the areas of highest pore concentration.

Pores have a defined size which is susceptible to measurement. Pore size is largely determined by genetic, environmental, and physiological factors. Visible pore diameter is often proportional to the size of subcutaneous sebaceous glands, and increased pore size is frequently associated with hyperactive sebaceous glands, including increased glandular activity and higher sebum production that occurs in adolescence, and with debris accumulation such as that observed in aging, when sebum production slows sufficiently to inhibit the constant stratum corneum shedding of normal youthful skin. Hyperactive sebaceous glands generate larger amounts of sebum which expands the pilary canal and dilates pore diameter to accommodate greater internal pressure. The aging process causes deterioration of the dermal elements surrounding the follicle. These changes are manifested by internal collapse of supporting skin structure and expansion of the follicular canal, resulting in pore dilation and greater visibility on the skin surface. The visual appearance of skin pores also partially depends upon the texture of surrounding surfaces. Rough skin scatters light in a manner which emphasizes openings on the skin surface, so pores appear larger.

Current treatments for enlarged pores are directed primarily to cleaning the skin to facilitate sebum and debris removal. Frequent washing is recommended for persons with oily skin, and washing with skin cleaners containing hydrating agents for persons with normal and dry skin. Sebum production is commonly curbed using drying agents such as alcohol and benzoyl peroxide.

It would be desirable to have alternative treatments for reducing skin pore size and improving overall skin appearance, particularly compositions that physically contract pores rather than just clean them.

SUMMARY OF THE INVENTION

The present invention overcomes deficiencies in the art by providing compositions that contract and reduce pore size. The compositions of the disclosure are also useful for collagen contraction of the skin, calming skin, and reducing oil on the skin.

In one aspect, there is disclosed a composition comprising: *Albizia julibrissin* bark extract; *Evodia rutaecarpa* fruit extract; hydrolyzed soy flour; sea whip extract; and a dermatologically acceptable vehicle. In some embodiments, the composition further comprises: glycerin; cyclopentasiloxane; polysilicone-11; pentaerythrityl tetraethylhexanoate; dipropylene glycol; methyl methacrylate crosspolymer; betaine; and bis-PEG/PPG-16/PPG-16/16 PEG/16 dimethicone. Alternatively, one or any combination said ingredients can be used in the compositions of the present invention. The amounts of the ingredients within the composition can vary (e.g., amounts can be as low as 0.000001% to as high as 80% w/w or any ranger therein). The vehicle may be any vehicle described herein and/or known in the art. In some embodiments, the composition is an emulsion, cream, lotion, solution, anhydrous base, or gel. In further embodiments, the composition is a solution. In some embodiments, the composition further comprises a solvent. The solvent may be a solvent known in the art or described herein. In some embodiments, the solvent is selected from one or more of isododecane, octyldodecanol, glycerin, propylene glycol, alcohol, denatured alcohol, propanediol, isohexadecane, ceteareth-33, 1,2-hexanediol, and water. In some embodiments, the composition comprises 0.1 to 1% by weight of *Albizia julibrissin* bark extract; 0.01 to 0.5% by weight of *Evodia rutaecarpa* fruit extract; 0.01 to 0.5% by weight of hydrolyzed soy flour; and 0.001 to 0.05% by weight of sea whip extract. In some embodiments, the composition further comprises: 3 to 10% by weight of glycerin; 2 to 8% by weight of cyclopentasiloxane; 1 to 6% by weight of polysilicone-11; 1 to 6% by weight of pentaerythrityl tetraethylhexanoate; 1 to 6% by weight of dipropylene glycol; 1 to 6% by weight of methyl methacrylate crosspolymer; 0.5 to 4% by weight of betaine; and 0.5 to 4% by weight of bis-PEG/PPG-16/PPG-16/16 PEG/16 dimethicone. In some embodiments, the composition comprises an effective amount of *Albizia julibrissin* bark extract capable of preventing glycation, reducing cutaneous signs of fatigue, reducing dark circles, reducing under eye bags, reducing dull complexion, reducing drawn features, supporting detoxifying of a glyoxalase and/or proteasome system, and/or protecting and repairing proteic structures damaged by glycation. In some embodiments, the composition comprises an effective amount of *Evodia rutaecarpa* fruit extract capable of reducing inflammation, reducing nociceptic pain, inhibiting PGE2, and/or reducing vasodilation. In some embodiments, the composition comprises an effective amount of hydrolyzed soy flour capable of reorganizing collagen fibers and/or protecting elastin from enzymatic degradation. In some embodiments, the composition comprises an effective amount of sea whip extract capable of reducing redness in skin, reducing inflammation, reducing the number of bacteria, reducing vaso-dilation, and/or neutralizing phospholipase A2. In some embodiments the composition comprises an effective amount of *Albizia julibrissin* bark extract, *Evodia rutaecarpa* fruit extract, hydrolyzed soy flour, and/or sea whip extract capable of reducing the size and/or appearance of pores, tightening skin, calming skin, and/or reducing skin oil. The composition may further comprise one or more ingredients described herein. For example, the composition may comprise one or more additional ingredients selected from one or more preservatives, emulsifiers, conditioning agents, thickening agents, fragrances, moisturizing agents, chelating agents, structuring agents, and colorants.

The compositions of the disclosure can be applied at least once, twice, three, four, or more times a day. Once applied, the composition can remain on the skin for at least 10, 20, 30, or 60 minutes, 1, 2, 3, 4, 5, 6, 7, 8, 9, 10, 11, or 12 hours, or longer. The compositions can also include any one of or any combination of cosmetic and/or pharmaceutical ingredients disclosed in this specification. For instance, compositions can include ingredients from at least one, two, three, four, five, six, seven, eight, nine, and/or ten of the following categories: (1) UV absorption agents; (2) moisturizing agents; (3) antioxidants; (4) structuring agents; (5) emulsifiers; (6) silicone containing compounds; (7) essential oils (8) thickening agents; (9) preservatives; and/or (10) conditioning agents. The amounts of such ingredients can range from 0.0001% to 99.9% by weight or volume of the composition, or any integer or range in between as disclosed in other sections of this specification.

It is also contemplated that the viscosity of the compositions can be selected to achieve a desired result (e.g., depending on the type of composition desired, the viscosity of such composition can be from about 1 cps to well over 1 million cps or any range or integer derivable therein (e.g., 2 cps, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000, cps, etc., as measured on a Brookfield Viscometer using a TC spindle at 2.5 rpm at 25° C.). The compositions in non-limiting aspects can have a pH of about 6 to about 9. In other aspects, the pH can be 1, 2, 3, 4, 5, 6, 7, 8, 9, 10, 11, 12, 13, or 14. In other aspects, the compositions can be sunscreens having a sun protection factor (SPF) of 1, 5, 10, 15, 20, 25, 30, 35, 40, 45, 50, 55, or more. The compositions can be sunscreen lotions, sprays, or creams. In particular aspects, the compositions can be oil-free, substantially anhydrous, and/or anhydrous. Other aspects include compositions having water.

Also disclosed are methods for using the compositions described herein. One aspect of the disclosure relates to a method for reducing skin pore size and/or appearance thereof comprising applying the composition of the disclosure to the skin.

A further method aspect relates to a method for tightening skin, calming skin, and/or reducing oil comprising applying a composition of the disclosure to the skin In some embodiments, the skin is cleansed prior to application of the composition. The compositions of the skin may be used after cleansing the skin and/or before the application of make-up to the skin. The compositions may be used on a daily basis for an extended period of time, such as, for example, every day for a week, every day for two weeks, every day for a month, every day for six months, every day for a year, or more. In certain aspects, the composition is applied to the skin and remains on the skin for at least 5, 10, 15, 30, or more minutes, or 1, 4, 8, 12, 16, 20, or 24 hours after topical application. The composition can be applied to leg skin, arm skin, torso skin, or skin in the pelvic region.

Additionally, the compositions can also be used to treat or prevent a variety of skin conditions. For instance, the compositions can be used to treat or prevent a fine line or wrinkle, erythema, sensitive skin, or inflamed skin. In particular aspects, erythema, sensitive skin, or inflamed skin is caused by skin sunburn, electrical treatments of skin, skin burns, contact allergies, systemic allergies, skin toxicity, exercise, insect stings, bacterial infection, viral infection, fungal infection, protozoa infection, massage, or windburn. In other aspects, the following additional skin conditions can be treated or prevented in accordance with the methods and compositions disclosed throughout the specification and claims: pruritus, lentigo, spider veins, age spots, senile purpura, keratosis, melasma, blotches, nodules, sun damaged skin, dermatitis (including, but not limited to seborrheic dermatitis, nummular dermatitis, contact dermatitis, atopic dermatitis, exfoliative dermatitis, perioral dermatitis, and stasis dermatitis), psoriasis, folliculitis, rosacea, acne, impetigo, erysipelas, erythrasma, eczema, and other inflammatory skin conditions. In certain non-limiting aspects, the skin condition can be caused by exposure to UV light, age, irradiation, chronic sun exposure, environmental pollutants, air pollution, wind, cold, heat, chemicals, disease pathologies, smoking, or lack of nutrition. The skin can be facial skin or non-facial skin (e.g., arms, legs, hands, chest, back, feet, etc.). The method can further comprise identifying a person in need of skin treatment. The person can be a male or female. The age of the person can be at least 1, 2, 3, 4, 5, 6, 7, 8, 9, 10, 15, 20, 25, 30, 35, 40, 45, 50, 55, 60, 65, 70, 75, 80, 85, 90, 95, or more years old, or any range derivable therein. The method can also include topically applying an amount effective to: increase the stratum corneum turnover rate of the skin; increase collagen synthesis in fibroblasts; increase cellular anti-oxidant defense mechanisms (e.g., exogenous additions of anti-oxidants can bolster, replenish, or prevent the loss of cellular antioxidants such as catalase and glutathione in skin cells (e.g., keratinocytes, melanocytes, langerhans cells, etc.) which will reduce or prevent oxidative damage to the skin, cellular, proteins, and lipids); inhibit melanin production in melanocytes; reduce or prevent oxidative damage to skin (including reducing the amount lipid peroxides and/or protein oxidation in the skin).

Also contemplated are kits that include any one of the compositions disclosed throughout the specification and claims. In certain embodiments, the composition is comprised in a container. The container can be a bottle, dispenser, or package. The container can dispense a predetermined amount of the composition. In certain aspects, the compositions is dispensed in a spray, dollop, or liquid. The container can include indicia on its surface. The indicia can be a word, an abbreviation, a picture, or a symbol.

Also contemplated is a product comprising a composition of the present invention. In non-limiting aspects, the product can be a cosmetic product. The cosmetic product can be those described in other sections of this specification or those known to a person of skill in the art. Non-limiting examples of products include a moisturizer, a cream, a lotion, a skin softener, a foundation, a night cream, a lipstick, a cleanser, a toner, a pore minimizer, a sunscreen, a mask, or an anti-aging product.

Also disclosed in the context of the present invention are Embodiments 1 to 20. Embodiment 1 is a composition comprising *Albizia julibrissin* bark extract, *Evodia rutaecarpa* fruit extract, hydrolyzed soy flour, sea whip extract, and a dermatologically acceptable vehicle. Embodiment 2 is the composition of Embodiment 1, wherein the composition comprises an effective amount of *Albizia julibrissin* bark extract capable of preventing glycation, reducing cutaneous signs of fatigue, reducing dark circles, reducing under eye bags, reducing dull complexion, reducing drawn features, supporting detoxifying of a glyoxalase and/or proteasome system, and/or protecting and repairing proteic structures damaged by glycation. Embodiment 3 is the composition of Embodiment 1, wherein the composition comprises an effective amount of *Evodia rutaecarpa* fruit extract capable of reducing inflammation, reducing nociceptic pain, inhibiting PGE2, and/or reducing vasodilation. Embodiment 4 is the composition of Embodiment 1, wherein the composition comprises an effective amount of hydrolyzed soy flour capable of reorganizing collagen fibers and/or protecting elastin from enzymatic degradation. Embodiment 5 is the composition of Embodiment 1, wherein the composition comprises an effective amount of sea whip extract capable of reducing redness in skin, reducing inflammation, reducing the number of bacteria, reducing vaso-dilation, and/or neutralizing phospholipase A2. Embodiment 6 is the composition of Embodiment 1, wherein the composition comprises an effective amount of *Albizia julibrissin* bark extract, *Evodia rutaecarpa* fruit extract, hydrolyzed soy flour, and/or sea whip extract capable of reducing the size and/or appearance of pores, tightening skin, calming skin, and/or reducing skin oil. Embodiment 7 is the composition of Embodiment 1 comprising 0.1 to 1% by weight of *Albizia julibrissin* bark extract, 0.01 to 0.5% by weight of *Evodia rutaecarpa* fruit extract, 0.01 to 0.5% by weight of hydrolyzed soy flour, and 0.001 to 0.05% by weight of sea whip extract. Embodiment 8 is the composition of Embodiment 1, further comprising glycerin, cyclopentasiloxane, polysilicone-11, pentaerythrityl tetraethylhexanoate, dipropylene glycol, methyl methacrylate crosspolymer, betaine, and bis-PEG/PPG-16/PPG-16/16 PEG/16 dimethicone. Embodiment 9 is the composition of Embodiment 8 comprising, 3 to 10% by weight of glycerin, 2 to 8% by weight of cyclopentasiloxane, 1 to 6% by weight of polysilicone-11, 1 to 6% by weight of pentaerythrityl tetraethylhexanoate, 1 to 6% by weight of dipropylene glycol, 1 to 6% by weight of methyl methacrylate crosspolymer, 0.5 to 4% by weight of betaine, and 0.5 to 4% by weight of bis-PEG/PPG-16/PPG-16/16 PEG/16 dimethicone. Embodiment 10 is the composition of Embodiment 1, further comprising a solvent. Embodiment 11 is the composition of Embodiment 10, wherein the solvent comprises one or more of isododecane, octyldodecanol, glycerin, propylene glycol, alcohol, denatured alcohol, propanediol, isohexadecane, ceteareth-33, 1,2-hexanediol, and water. Embodiment 12 is the composition of Embodiment 1, wherein the composition is an emulsion, cream, lotion, solution, anhydrous base, or gel. Embodiment 13 is the composition of Embodiment 12, wherein the composition is a solution. Embodiment 14 is the composition of Embodiment 1, further comprising one or more additional ingredients selected from one or more preservatives, emulsifiers, conditioning agents, thickening agents, fragrances, moisturizing agents, chelating agents, structuring agents, and colorants. Embodiment 15 is a method for reducing skin pore size and/or appearance thereof comprising applying the composition of Embodiment 1 to the skin. Embodiment 16 is the method of Embodiment 15, wherein the skin is cleansed prior to application of the composition. Embodiment 17 is the method of Embodiment 15 wherein the composition is applied daily. Embodiment 18 is a method for tightening skin, calming skin, and/or reducing oil comprising applying the composition of Embodiment 1 to the skin. Embodiment 19 is the method of Embodiment 18, wherein the skin is cleansed prior to application of the composition. Embodiment 20 is the method of Embodiment 18, wherein the composition is applied daily.

The compositions and methods for their use can "comprise," "consist essentially of," or "consist of" any of the ingredients disclosed throughout the specification. As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

"Consisting essentially of" means that inclusion of additional ingredients in the compositions do not materially affect the beneficial properties of the compositions. For instance, if a composition "consists essentially of" *Albizia julibrissin* bark extract; *Evodia rutaecarpa* fruit extract; hydrolyzed soy flour; and sea whip extract, said composition excludes any ingredients that would materially affect the beneficial properties of the compositions for reducing the size and/or appearance of pores or for tightening skin, calming skin, and/or reducing oil.

It is contemplated that any embodiment discussed in this specification can be implemented with respect to any method or composition of the invention, and vice versa. Furthermore, compositions of the invention can be used to achieve methods of the invention.

In some embodiments, compositions of the present invention can be pharmaceutically or cosmetically elegant. "Pharmaceutically elegant" and/or "cosmetically elegant" describes a composition that has particular tactile properties which feel pleasant on the skin (e.g., compositions that are not too watery or greasy, compositions that have a silky texture, compositions that are non-tacky or sticky, etc.). Pharmaceutically or cosmetically elegant can also relate to the creaminess or lubricity properties of the composition or to the moisture retaining properties of the composition.

"Topical application" means to apply or spread a composition onto the surface of keratinous tissue. "Topical skin composition" includes compositions suitable for topical application on keratinous tissue. Such compositions are typically dermatologically-acceptable in that they do not have undue toxicity, incompatibility, instability, allergic response, and the like, when applied to skin. Topical skin care compositions of the present invention can have a selected viscosity to avoid significant dripping or pooling after application to skin.

"Keratinous tissue" includes keratin-containing layers disposed as the outermost protective covering of mammals and includes, but is not limited to, skin, hair and nails.

The term "about" or "approximately" are defined as being close to as understood by one of ordinary skill in the art, and in one non-limiting embodiment the terms are defined to be within 10%, preferably within 5%, more preferably within 1%, and most preferably within 0.5%.

The term "substantially" and its variations are defined as being largely but not necessarily wholly what is specified as understood by one of ordinary skill in the art, and in one non-limiting embodiment substantially refers to ranges within 10%, within 5%, within 1%, or within 0.5%.

The terms "inhibiting," "reducing," "treating," or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

DESCRIPTION OF ILLUSTRATIVE EMBODIMENTS

The compositions described herein are useful for reducing the size and/or appearance of pores or for tightening skin, calming skin, and/or reducing oil. The compositions described herein may also be used to impart a fragrance, shine, or protectant film to the skin.

The present invention is premised on a discovery of a combination of ingredients—Sea Whip Extract, *Evodia rutaecarpa* fruit extract, Hydrolyzed soy flour, and/or *Albizia julibrissin* bark extract—that can be used to reduce the size and/or appearance of pores or to tighten skin, calm skin, and to reduce skin oil. These ingredients are discussed in more detail below.

Sea whip extract is an extract of the marine invertebrate, *Pseudopterogorgia elisabethae*. It is known for possessing anti-inflammatory and antibacterial properties. It is also known as gorgonian extract and can be beneficial in reducing redness in skin due to vaso-dilation. Without being bound to any scientific theory, it is believed that sea whip extract reduces redness in skin by neutralizing phospholipase A2, a naturally occurring enzyme in the body that can lead to pain and swelling in the skin. In some embodiments, this ingredient is sold by Lipochemicals.

*Evodia rutaecarpa* fruit extract is known for its anti-inflammatory properties and also has anti-nociceptive activity. The *Evodia rutaecarpa* fruit extract was found to be a potent inhibitor of UVB-induced prostoaglandin E2 (PGE2), a vasodilator, released by keratinocytes in cell culture. In some embodiments, this ingredient is sold by Gattefosse under the trade name of Gatuline® Radiance.

Hydrolyzed soy flour is used as a skin conditioning agent in cosmetic compositions. It is known to have high glycoprotein and structural polysaccharide content that are able to reorganize collagen fibers and also protect elastin from enzymatic degradation. In some embodiments, this ingredient is sold by Silab under the trade name of Raffermine® 2.

*Albizia julibrissin* bark extract is also known as the Persian or pink silk tree and is native to Southwestern and Eastern Asia. It is used in cosmetic compositions as a fragrance and has also been found to prevent glycation. *Albizia julibrissin* bark extract promotes a visible reduction in the cutaneous signs of fatigue such as dark circles, under eye bags, dull complexion and drawn features. It is supportive of detoxifying systems such as glyoxalase and the proteasome, and can protect and repair the proteic structures damaged by glycation. In some embodiments, this ingredient is sold by Sederma under the trade name of Prodizia™.

The extracts described herein can be extracts made through extraction methods known in the art and combinations thereof. Non-limiting examples of extraction methods include the use of liquid-liquid extraction, solid phase extraction, aqueous extraction, ethyl acetate, alcohol, acetone, oil, supercritical carbon dioxide, heat, pressure, pressure drop extraction, ultrasonic extraction, etc. Extracts can be a liquid, solid, dried liquid, re-suspended solid, etc.

A. Compositions of the Present Invention

It is contemplated that the compositions of the present invention can include any cosmetic ingredient or any combination thereof described throughout this specification. The concentrations of the any ingredient within the compositions can vary. In non-limiting embodiments, for example, the compositions can comprise, consisting essentially of, or consist of, in their final form, for example, at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.0550%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or any range derivable therein, of at least one of the ingredients that are mentioned throughout the specification and claims. In non-limiting aspects, the percentage can be calculated by weight or volume of the total composition. A person of ordinary skill in the art would understand that the concentrations can vary depending on the addition, substitution, and/or subtraction of ingredients in a given composition.

The disclosed compositions of the present invention may also include various antioxidants to retard oxidation of one or more components. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof. In some embodiments, the compositions do not contain parabens.

B. Vehicles

The compositions of the present invention can be incorporated into all types of vehicles (i.e. dermatologically acceptable). Non-limiting examples of suitable vehicles include emulsions (e.g., water-in-oil, water-in-oil-in-water, oil-in-water, silicone-in-water, water-in-silicone, oil-in-water-in-oil, oil-in-water-in-silicone emulsions), creams, lotions, solutions (both aqueous and hydro-alcoholic), anhydrous bases (such as lipsticks and powders), gels, and ointments or by other method or any combination of the forgoing as would be known to one of ordinary skill in the art (Remington's, 1990). Variations and other appropriate vehicles will be apparent to the skilled artisan and are appropriate for use in the present invention. In certain aspects, it is important that the concentrations and combinations of the compounds, ingredients, and agents be selected in such a way that the combinations are chemically compatible and do not form complexes which precipitate from the finished product.

It is also contemplated that ingredients identified throughout this specification can be individually or combinatorially encapsulated for delivery to a target area such as skin. Non-limiting examples of encapsulation techniques include the use of liposomes, vesicles, and/or nanoparticles (e.g., biodegradable and non-biodegradable colloidal particles comprising polymeric materials in which the ingredient is trapped, encapsulated, and/or absorbed—examples include nanospheres and nanocapsules) that can be used as delivery vehicles to deliver the ingredient to skin (see, e.g., U.S. Pat. No. 6,387,398; U.S. Pat. No. 6,203,802; U.S. Pat. No. 5,411,744; Kreuter 1998).

C. Cosmetic Products and Articles of Manufacture

The composition of the present invention can also be used in many cosmetic products including, but not limited to, sunscreen products, sunless skin tanning products, hair products, finger nail products, moisturizing creams, skin benefit creams and lotions, softeners, day lotions, gels, ointments, foundations, night creams, lipsticks, cleansers, toners, masks, or other known cosmetic products or applications. Additionally, the cosmetic products can be formulated as leave-on or rinse-off products. In certain aspects, the compositions of the present invention are stand-alone products.

D. Additional Ingredients

In addition to the specific combination of ingredients disclosed herein, compositions of the present invention can include additional ingredients such as cosmetic ingredients and pharmaceutical active ingredients. Non-limiting examples of these additional ingredients are described in the following subsections.

1. Cosmetic Ingredients

The CTFA International Cosmetic Ingredient Dictionary and Handbook (2004 and 2008) describes a wide variety of non-limiting cosmetic ingredients that can be used in the context of the present invention. Examples of these ingredient classes include: fragrances (artificial and natural; e.g. gluconic acid, phenoxyethanol, triethyl citrate, and triethanolamine), dyes and colorants (e.g., Blue 1, Blue 1 Lake, Red 40, Red 28 Lake, Red 7 Lake, Red 6 Lake, titanium dioxide, Unipure Red 6, Unipure Red 28, Unipure Red 33, Unipure Yellow OX, Unipure Yellow 5, FD&C blue 1, D&C blue no. 4, D&C green no. 5, D&C orange no. 4, D&C red no. 17, D&C red no. 6, D&C red no. 7, D&C red no. 30, D&C red no. 33, D&C violet no. 2, D&C yellow no. 10, D&C yellow no. 11, iron oxides, chromium oxides, tin oxide, ultramarines, and mica), flavoring agents (e.g. *Stevia rebaudiana* (sweetleaf) extract), adsorbents, lubricants, solvents (e.g. water, hydrocarbons, hexylene glycol, isododecane, octyldodecanol, glycerin, and propylene glycol), moisturizers (including, e.g., emollients, humectants, film formers, occlusive agents, and agents that affect the natural moisturization mechanisms of the skin), water-repellants, UV absorbers (physical and chemical absorbers such as paraaminobenzoic acid ("PABA") and corresponding PABA derivatives, titanium dioxide, zinc oxide, etc.), essential oils, vitamins (e.g. A, B, C, D, E, and K), trace metals (e.g. zinc, calcium and selenium), inorganic salts (e.g. sodium chloride, magnesium nitrate, and magnesium chloride), anti-irritants (e.g. steroids and non-steroidal anti-inflammatories), botanical extracts (e.g. aloe vera, chamomile, cucumber extract, ginkgo biloba, ginseng, and rosemary), anti-microbial agents, antioxidants (e.g., BHT and tocopherol), chelating agents (e.g., disodium EDTA and tetrasodium EDTA), preservatives (e.g., methylparaben and propylparaben), pH adjusters (e.g., sodium hydroxide, triethanolamine, and citric acid), absorbents (e.g., aluminum starch octenylsuccinate, kaolin, corn starch, oat starch, cyclodextrin, talc, and zeolite), skin bleaching and lightening agents (e.g., hydroquinone and niacinamide lactate), humectants (e.g., sorbitol, urea, and manitol), exfoliants, waterproofing agents (e.g., magnesium/aluminum hydroxide stearate), conditioning agents (e.g., aloe extracts, allantoin, bisabolol, ceramides, dimethicone, hyaluronic acid, and dipotassium glycyrrhizate), and film formers (e.g. acrylates copolymer and polyquarternium-7). Non-limiting examples of some of these ingredients are provided in the following subsections.

a. UV Absorption Agents

UV absorption agents that can be used in combination with the compositions of the present invention include chemical and physical sunblocks. Non-limiting examples of chemical sunblocks that can be used include para-aminobenzoic acid (PABA), PABA esters (glyceryl PABA, amyldimethyl PABA and octyldimethyl PABA), butyl PABA, ethyl PABA, ethyl dihydroxypropyl PABA, benzophenones (oxybenzone, sulisobenzone, benzophenone, and benzophenone-1 through 12), cinnamates (octyl methoxycinnamate, isoamyl p-methoxycinnamate, octylmethoxy cinnamate, cinoxate, diisopropyl methyl cinnamate, DEA-methoxycinnamate, ethyl diisopropylcinnamate, glyceryl octanoate dimethoxycinnamate and ethyl methoxycinnamate), cinnamate esters, salicylates (homomethyl salicylate, benzyl salicylate, glycol salicylate, isopropylbenzyl salicylate, etc.), anthranilates, ethyl urocanate, homosalate, octisalate, oxtinoxate, dibenzoylmethane derivatives (e.g., avobenzone), octocrylene, octyl triazone, digalloy trioleate, glyceryl aminobenzoate, lawsone with dihydroxyacetone, ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis diethylamino hydroxybenzoyl benzoate, bis benzoxazoylphenyl ethylhexylimino triazine, drometrizole trisiloxane, methylene bis-benzotriazolyl tetramethylbutyiphenol, and bis-ethylhexyloxyphenol methoxyphenyltriazine, 4-methylbenzylidenecamphor, and isopentyl 4-methoxycinnamate. Non-limiting examples of physical sunblocks include, kaolin, talc, petrolatum and metal oxides (e.g., titanium dioxide and zinc oxide).

b. Moisturizing Agents

Non-limiting examples of moisturizing agents that can be used with the compositions of the present invention include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, salts of pyrollidone carboxylic acid, potassium PCA, propylene glycol, sodium glucuronate, sodium PCA, sorbitol, sucrose, trehalose, urea, and xylitol.

Other examples include acetylated lanolin, acetylated lanolin alcohol, alanine, algae extract, *aloe barbadensis*, *aloe-barbadensis* extract, *aloe barbadensis* gel, *althea officinalis* extract, apricot (*prunus armeniaca*) kernel oil, arginine, arginine aspartate, *arnica montana* extract, aspartic acid, avocado (*persea gratissima*) oil, barrier sphingolipids, butyl alcohol, beeswax, behenyl alcohol, beta-sitosterol, birch (*betula alba*) bark extract, borage (*borago officinalis*) extract, butcherbroom (*ruscus aculeatus*) extract, butylene glycol, *calendula officinalis* extract, *calendula officinalis* oil, candelilla (*euphorbia cerifera*) wax, canola oil, caprylic/capric triglyceride, cardamon (*elettaria cardamomum*) oil, carnauba (*copernicia cerifera*) wax, carrot (*daucus carota sativa*) oil, castor (*ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*anthemis nobilis*) oil, cholesterol, cholesterol esters, cholesteryl hydroxystearate, citric acid, clary (*salvia sclarea*) oil, cocoa (*theobroma cacao*) butter, coco-caprylate/caprate, coconut (*cocos nucifera*) oil, collagen, collagen amino acids, corn (*zea mays*) oil, fatty acids, decyl oleate, dimethicone copolyol, dimethiconol, dioctyl adipate, dioctyl succinate, dipentaerythrityl hexacaprylate/hexacaprate, DNA, erythritol, ethoxydiglycol, ethyl linoleate, *eucalyptus globulus* oil, evening primrose (*oenothera biennis*) oil, fatty acids, geranium *maculatum* oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*vitis vinifera*) seed oil, hazel (*corylus americana*) nut oil, hazel (*corylus avellana*) nut oil, hexylene glycol, hyaluronic acid, hybrid safflower (*carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*jasminum officinale*) oil, jojoba (*buxus chinensis*) oil, kelp, kukui (*aleurites moluccana*) nut oil, lactamide MEA, laneth-16, laneth-10 acetate, lanolin, lanolin acid, lanolin alcohol, lanolin oil, lanolin wax, lavender (*lavandula angustifolia*) oil, lecithin, lemon (*citrus medica limonum*) oil, linoleic acid, linolenic acid, *macadamia ternifolia* nut oil, maltitol, *matricaria* (*chamomilla recutita*) oil, methyl glucose sesquistearate, methylsilanol PCA, mineral oil, mink oil, *mortierella* oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*olea europaea*) oil, orange (*citrus aurantium dulcis*) oil, palm (*elaeis guineensis*) oil, palmitic acid, pantethine, panthenol, panthenyl ethyl ether, paraffin, PCA, peach (*prunus persica*) kernel oil, peanut (*arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG40 sorbitan peroleate, PEG-5 soy sterol, PEG-10 soy sterol, PEG-2 stearate, PEG-8 stearate, PEG-20 stearate, PEG-32 stearate, PEG40 stearate, PEG-50 stearate, PEG-100 stearate, PEG-150 stearate, pentadecalactone, peppermint (*mentha piperita*) oil, petrolatum, phospholipids, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, retinol, retinol palmitate, rice (*oryza sativa*) bran oil, RNA, rosemary (*rosmarinus officinalis*) oil, rose oil, safflower (*carthamus tinctorius*) oil, sage (*salvia officinalis*) oil, sandalwood (*santalum album*) oil, serine, serum protein, sesame (*sesamum indicum*) oil, shea butter (*butyrospermum parkii*), silk powder, sodium chondroitin sulfate, sodium hyaluronate, sodium lactate, sodium palmitate, sodium PCA, sodium polyglutamate, soluble collagen, sorbitan laurate, sorbitan oleate, sorbitan palmitate, sorbitan sesquioleate, sorbitan stearate, sorbitol, soybean (*glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*helianthus annuus*) seed oil, sweet almond (*prunus amygdalus dulcis*) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (*triticum vulgare*) germ oil, and ylang ylang (*cananga odorata*) oil.

c. Antioxidants

Non-limiting examples of antioxidants that can be used with the compositions of the present invention include acetyl cysteine, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCI, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

d. Structuring Agents

In other non-limiting aspects, the compositions of the present invention can include a structuring agent. Structuring agent, in certain aspects, assist in providing rheological characteristics to the composition to contribute to the composition's stability. In other aspects, structuring agents can also function as an emollient, emulsifier or surfactant. Non-limiting examples of structuring agents include stearic acid, palmitic acid, stearyl alcohol, cetyl alcohol, PPG-30 cetyl ether, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, polyoxyethylene methylglucoside dioleate, tea-lauryl sulfate, polyethylene glycol ester of stearic acid, $C_{12-15}$ alkyl benzoate, propylene glycol myristyl ether acetate, 3-hydroxypropyl (E)-octadec-9-enoate, sorbitan laurate, sorbitan stearate, carbomer, ammonium acryloyldimethyltaurate/carboxyethyl acrylate crosspolymer, sodium laureth sulfate, hydroxypropyl cyclodextrin, PPG-26 oleate, and mixtures thereof.

e. Emulsifiers

In certain aspects of the present invention, the compositions do not include an emulsifier. In other aspects, however, the compositions can include one or more emulsifiers. Emulsifiers can reduce the interfacial tension between phases and improve the formulation and stability of an emulsion. The emulsifiers can be nonionic, cationic, anionic, and zwitterionic emulsifiers (See McCutcheon's (1986); U.S. Pat. Nos. 5,011,681; 4,421,769; 3,755,560). Non-limiting examples include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), sorbitan isostearate, polyethylene glycol 5 soya sterol, steareth-2, steareth-20, steareth-21, ceteareth-20, PPG-2 methyl glucose ether distearate, ceteth-10, polysorbate 80, cetyl phosphate, potassium cetyl phosphate, diethanolamine cetyl phosphate, polysorbate 60, glyceryl stearate, PEG-100 stearate, C20-40 alcohols, hydroxyethyl acrylate/sodium acryloyldimethyl taurate copolymer, and mixtures thereof.

f. Silicone Containing Compounds

In non-limiting aspects, silicone containing compounds include any member of a family of polymeric products whose molecular backbone is made up of alternating silicon and oxygen atoms with side groups attached to the silicon atoms. By varying the —Si—O— chain lengths, side groups, and crosslinking, silicones can be synthesized into a wide variety of materials. They can vary in consistency from liquid to gel to solids.

The silicone containing compounds that can be used in the context of the present invention include those described in this specification or those known to a person of ordinary skill in the art. Non-limiting examples include silicone oils (e.g., volatile and non-volatile oils), gels, and solids. In certain aspects, the silicon containing compounds includes a silicone oils such as a polyorganosiloxane. Non-limiting examples of polyorganosiloxanes include dimethicone, cyclomethicone, polysilicone-11, phenyl trimethicone, trimethylsilylamodimethicone, stearoxytrimethylsilane, or mixtures of these and other organosiloxane materials in any given ratio in order to achieve the desired consistency and application characteristics depending upon the intended application (e.g., to a particular area such as the skin, hair, or eyes). A "volatile silicone oil" includes a silicone oil have a low heat of vaporization, i.e. normally less than about 50 cal per gram of silicone oil. Non-limiting examples of volatile silicone oils include: cyclomethicones such as Dow Corning 344 Fluid, Dow Corning 345 Fluid, Dow Corning 244 Fluid, and Dow Corning 245 Fluid, Volatile Silicon 7207 (Union Carbide Corp., Danbury, Conn.); low viscosity dimethicones, i.e. dimethicones having a viscosity of about 50 cst or less (e.g., dimethicones such as Dow Corning 200-0.5 cst Fluid). The Dow Corning Fluids are available from Dow Corning Corporation, Midland, Mich. Cyclomethicone and dimethicone are described in the Third Edition of the CTFA Cosmetic Ingredient Dictionary (incorporated by reference) as cyclic dimethyl polysiloxane compounds and a mixture of fully methylated linear siloxane polymers end-blocked with trimethylsiloxy units, respectively. Silicone containing compounds of the invention may also be used as bulking agents (e.g. silicic acid and aluminum calcium sodium silicate). Other non-limiting volatile silicone oils that can be used in the context of the present invention include those available from General Electric Co., Silicone Products Div., Waterford, N.Y. and SWS Silicones Div. of Stauffer Chemical Co., Adrian, Mich.

g. Essential Oils

Essential oils include oils derived from herbs, flowers, trees, and other plants. Such oils are typically present as tiny droplets between the plant's cells, and can be extracted by several methods known to those of skill in the art (e.g., steam distilled, enfleurage (i.e., extraction by using fat), maceration, solvent extraction, or mechanical pressing). When these types of oils are exposed to air they tend to evaporate (i.e., a volatile oil). As a result, many essential oils are colorless, but with age they can oxidize and become darker. Essential oils are insoluble in water and are soluble in alcohol, ether, fixed oils (vegetal), and other organic solvents. Typical physical characteristics found in essential oils include boiling points that vary from about 160° to 240° C. and densities ranging from about 0.759 to about 1.096.

Essential oils typically are named by the plant from which the oil is found. For example, rose oil or peppermint oil are derived from rose or peppermint plants, respectively. Non-limiting examples of essential oils that can be used in the context of the present invention include sesame oil, *macadamia* nut oil, tea tree oil, evening primrose oil, Spanish sage oil, Spanish rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, *eucalyptus* oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, or ylang ylang. Other essential oils known to those of skill in the art are also contemplated as being useful within the context of the present invention.

h. Thickening Agents

Thickening agents, including thickener or gelling agents, include substances which that can increase or control the viscosity of a composition. Thickeners includes those that can increase the viscosity of a composition without substantially modifying the efficacy of the active ingredient within the composition. Thickeners can also increase the stability of the compositions of the present invention. In certain aspects of the present invention, thickeners include hydrogenated polyisobutene or trihydroxystearin, or a mixture of both.

Non-limiting examples of additional thickening agents that can be used in the context of the present invention include carboxylic acid polymers, crosslinked polyacrylate polymers, polyacrylamide polymers, polysaccharides, and gums. Examples of carboxylic acid polymers include crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (see U.S. Pat. Nos. 5,087,445; 4,509,949; 2,798,053; CTFA International Cosmetic Ingredient Dictionary, Fourth edition, 1991, pp. 12 and 80). Examples of commercially available carboxylic acid polymers include carbomers, which are homopolymers of acrylic acid crosslinked with allyl ethers of sucrose or pentaerytritol (e.g., Carbopol™ 900 series from B. F. Goodrich).

Non-limiting examples of crosslinked polyacrylate polymers include cationic and nonionic polymers. Examples are described in U.S. Pat. Nos. 5,100,660; 4,849,484; 4,835,206; 4,628,078; 4,599,379.

Non-limiting examples of polyacrylamide polymers (including nonionic polyacrylamide polymers including substituted branched or unbranched polymers) include polyacrylamide, isoparaffin and laureth-7, multi-block copolymers of acrylamides and substituted acrylamides with acrylic acids and substituted acrylic acids.

Non-limiting examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (preferably hydroxy ethylated or hydroxypropylated) to form a hydroxyalkylated cellulose which is then further modified with a $C_{10}$-$C_{30}$ straight chain or branched chain alkyl group through an ether linkage. Typically these polymers are ethers of $C_{10}$-$C_{30}$ straight or branched chain alcohols with hydroxyalkylcelluloses. Other useful polysaccharides include scleroglucans comprising a linear chain of (1-3) linked glucose units with a (1-6) linked glucose every three unit.

Non-limiting examples of gums that can be used with the present invention include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, *sclerotium* gum, sodium carboxymethyl dextran, sodium carrageenan, tragacanth gum, xanthan gum, and mixtures thereof.

Further non-limiting examples of thickening agents include carbomer, cetyl alcohol, ammonium acryloydimethyltaurate/VP copolymer, aluminum starch actenylsuccinate, cocamidopropyl betaine, PPG-2 hydroxyethyl coco/isostearamide, tin oxide, hexadecane copolymer, calcium aluminum borosilicate, alumina, calcium sodium borosilicate, aluminum calcium sodium silicate, magnesium aluminum silicate, synthetic fluorphlogopite, and disodium EDTA.

i. Preservatives

Non-limiting examples of preservatives that can be used in the context of the present invention include quaternary ammonium preservatives such as polyquaternium-1 and benzalkonium halides (e.g., benzalkonium chloride ("BAC") and benzalkonium bromide), parabens (e.g., methylparabens and propylparabens), benzyl alcohol, chlorobutanol, phenol, sorbic acid, thimerosal, caprylyl glycol, iodopropynyl butylcarbamate, methylisothiazolinone, methylchloroisothiazolinone, sodium benzoate, dimethylol-5,5-dimethylhydantoin, 3-iodo-2-propynyl butyl carbamate, phenoxyethanol, caprylyl alcohol, ethylhexyl glycerin, hexylene glycol, DMDM hydantoin, chlorphenesin, decylene glycol, and combinations thereof.

j. Conditioning Agents

Non-limiting examples of conditioning agents that can be used in the context of the present invention include caprylyl glycol, ethylhexylglycerin, PEG-12 dimethicone, hydroxypropyl cyclodextrin, dimethicone, tocopheryl acetate, *Butyrospermum parkii* (shea butter), polymers of polyethylene glycol and methicone, *Helianthus annuus* (sunflower) seed oil, PEG-18 glyceryl oleate/cocoate, cyclotetrasiloxane, cyclohexasiloxane, cyclopentasiloxane, tocopherol, glycerin, *Carthamus tinctorius* (safflower) oleosomes, butylene glycol, allantoin, hydrogenated palm kernel oil, caprylic/capric triglyceride, propylene glycol stearate, panthenol, polypropylene glycol ether of cetyl alcohol, polyquaternium-7, ethoxylated glyceryl esters, ethylhexyl palmitate. aloe extracts, bisabolol, ceramides, hyaluronic acid, dipotassium glycyrrhizate, cocamidopropyl betaine, pentaerythrityl tetraisostearate, glyceryl behenate/eicosadioate, tridecyl trimellitate, *Albizia julibrissin* bark extract, *Evodia rutaecarpa* fruit extract, hydrolyzed soy flour, *Lavandula angustifolia* (lavender) flower/leaf/stem extract, sea whip extract, *Elettaria cardamomum* seed extract, *Rubus idaeus* (raspberry) fruit extract, *Pyrus malus* (apple) fruit extract, *Camellia sinensis* leaf extract, *Cananga odorata* flower extract, *Cupressus sempervirens* leaf/stem extact, *santalum album* (sandalwood) wood extract, *Coffea Arabica* (coffee) seed extract, *Citrus Aurantium amara* (bitter orange) flower extract, *Cucumis melo cantalupensis* fruit extract, rose extract, *Salvia officinalis* (sage) leaf extract, *Fucus vesiculosus* extract, *Rosemarinus officinalis* (rosemary) leaf extract, *Jasminum officinale* (jasmine) flower extract, *Cucumis sativus* (cucumber) fruit extract, and mixtures thereof.

2. Pharmaceutical Ingredients

Pharmaceutical active agents are also contemplated as being useful with the compositions of the present invention. Non-limiting examples of pharmaceutical active agents include anti-acne agents, agents used to treat rosacea, analgesics, anesthetics, anorectals, antihistamines, anti-inflammatory agents including non-steroidal anti-inflammatory drugs, antibiotics, antifungals, antivirals, antimicrobials, anti-cancer actives, scabicides, pediculicides, antineoplastics, antiperspirants, antipruritics, antipsoriatic agents, antiseborrheic agents, biologically active proteins and peptides, burn treatment agents, cauterizing agents, depigmenting agents, depilatories, diaper rash treatment agents, enzymes, hair growth stimulants, hair growth retardants including DFMO and its salts and analogs, hemostatics, kerotolytics, canker sore treatment agents, cold sore treatment agents, dental and periodontal treatment agents, photosensitizing actives, skin protectant/barrier agents, steroids including hormones and corticosteroids, sunburn treatment agents, sunscreens, transdermal actives, nasal actives, vaginal actives, wart treatment agents, wound treatment agents, wound healing agents, etc.

E. Kits

Kits are also contemplated as being used in certain aspects of the present invention. For instance, compositions of the present invention can be included in a kit. A kit can include a container. Containers can include a bottle, a metal tube, a laminate tube, a plastic tube, a dispenser, a pressurized container, a barrier container, a package, a compartment, a lipstick container, a compact container, cosmetic pans that can hold cosmetic compositions, or other types of containers such as injection or blow-molded plastic containers into which the dispersions or compositions or desired bottles, dispensers, or packages are retained. The kit and/or container can include indicia on its surface. The indicia, for example, can be a word, a phrase, an abbreviation, a picture, or a symbol.

The containers can dispense a pre-determined amount of the composition. In other embodiments, the container can be squeezed (e.g., metal, laminate, or plastic tube) to dispense a desired amount of the composition. The composition can be dispensed as a spray, an aerosol, a liquid, a fluid, or a semi-solid. The containers can have spray, pump, or squeeze mechanisms. A kit can also include instructions for employing the kit components as well the use of any other compositions included in the container. Instructions can include an explanation of how to apply, use, and maintain the compositions.

EXAMPLES

The following examples are included to demonstrate certain non-limiting aspects of the invention. It should be appreciated by those of skill in the art that the techniques disclosed in the examples which follow represent techniques discovered by the inventor to function well in the practice of the invention. However, those of skill in the art should, in light of the present disclosure, appreciate that many changes can be made in the specific embodiments which are disclosed and still obtain a like or similar result without departing from the spirit and scope of the invention.

Example 1

Non-Limiting Examples of Compositions

The compositions listed in Tables 1-3 are non-limiting compositions that can be used in the context of the present invention.

TABLE 1*

| Ingredient** | % Concentration (by weight) |
| --- | --- |
| Water | 65 |
| Glycerin | 6 |
| Cyclopentasiloxane | 5 |
| Polysilicone-11 | 3 |
| Pentaerythrityl Tetraethylhexanoate | 3.5 |
| Dipropylene Glycol | 3 |
| Methyl Methacrylate Crosspolymer | 3 |
| Betaine | 2 |
| Bis-PEG/PPG-16/PPG-16/16 PEG/16 Dimethicone | 2 |
| *Albizia julibrissin* bark extract | 0.5 |
| *Evodia rutaecarpa* fruit extract | 0.1 |
| Hydrolyzed soy flour | 0.02 |
| Sea whip extract | 0.01 |
| Excipients*** | q.s. |

*Formulation can be prepared by mixing the ingredients in a beaker under heat 70-75° C. until homogenous. Subsequently, the formulation can be cooled to standing room temperature (20-25° C.). Further, and if desired, additional ingredients can be added, for example, to modify the rheological properties of the composition.
**Any of the additional ingredients (or combination thereof) described in the specification can be used.
***Excipients can be added, for example, to modify the rheological properties of the composition. Alternatively, the amount of water can be varied so long as the amount of water in the composition is at least 60% w/w, and preferably between 60 to 85% w/w.

TABLE 2*

| Ingredient** | % Concentration (by weight) |
| --- | --- |
| Water | 65 |
| Glycerin | 7 |
| Cyclopentasiloxane | 5 |
| Polysilicone-11 | 4 |
| Pentaerythrityl Tetraethylhexanoate | 4 |
| Dipropylene Glycol | 3 |
| Methyl Methacrylate Crosspolymer | 3 |
| Betaine | 2 |
| Bis-PEG/PPG-16/PPG-16/16 PEG/16 Dimethicone | 2 |
| *Albizia julibrissin* bark extract | 0.6 |
| *Evodia rutaecarpa* fruit extract | 0.05 |
| Hydrolyzed soy flour | 0.01 |
| Sea whip extract | 0.01 |
| Propanediol | 1 |
| Isohexadecane | 0.5 |
| Excipients*** | q.s. |

*Formulation can be prepared by mixing the ingredients in a beaker under heat 70-75° C. until homogenous. Subsequently, the formulation can be cooled to standing room temperature (20-25° C.). Further, and if desired, additional ingredients can be added, for example, to modify the rheological properties of the composition.
**Any of the additional ingredients (or combination thereof) described in the specification can be used.
***Excipients can be added, for example, to modify the rheological properties of the composition. Alternatively, the amount of water can be varied so long as the amount of water in the composition is at least 60% w/w, and preferably between 60 to 85% w/w.

TABLE 3*

| Ingredient** | % Concentration (by weight) |
| --- | --- |
| Water | 65 |
| Glycerin | 6 |
| Cyclopentasiloxane | 5 |
| Polysilicone-11 | 3 |
| Pentaerythrityl Tetraethylhexanoate | 3 |
| Dipropylene Glycol | 3 |
| Methyl Methacrylate Crosspolymer | 3 |
| Betaine | 2 |
| Bis-PEG/PPG-16/PPG-16/16 PEG/16 Dimethicone | 1 |
| *Albizia julibrissin* bark extract | 0.6 |
| *Evodia rutaecarpa* fruit extract | 0.1 |
| Hydrolyzed soy flour | 0.02 |
| Sea whip extract | 0.005 |
| Propanediol | 1 |
| Isohexadecane | 0.5 |
| 1,2-Hexanediol | 0.1 |
| Excipients*** | q.s. |

*Formulation can be prepared by mixing the ingredients in a beaker under heat 70-75° C. until homogenous. Subsequently, the formulation can be cooled to standing room temperature (20-25° C.). Further, and if desired, additional ingredients can be added, for example, to modify the rheological properties of the composition.
**Any of the additional ingredients (or combination thereof) described in the specification can be used.
***Excipients can be added, for example, to modify the rheological properties of the composition. Alternatively, the amount of water can be varied so long as the amount of water in the composition is at least 60% w/w, and preferably between 60 to 85% w/w.

Example 2

Assays

The efficacy of the combination of ingredients disclosed throughout the specification and claims can be determined by using the following assays.

Erythema Assay:

An assay to measure the reduction of skin redness can be evaluated using a Minolta Chromometer. Skin erythema may be induced by applying a 0.2% solution of sodium dodecyl sulfate on the forearm of a subject. The area is protected by an occlusive patch for 24 hrs. After 24 hrs, the patch is removed and the irritation-induced redness can be assessed using the a* values of the Minolta Chroma Meter.

The a* value measures changes in skin color in the red region. Immediately after reading, the area is treated with a composition of the present invention. Repeat measurements are taken at regular intervals to determine the formula's ability to reduce redness and irritation.

Skin Moisture/Hydration Assay:

Skin moisture/hydration benefits can be measured by using impedance measurements with the Nova Dermal Phase Meter. The impedance meter measures changes in skin moisture content. The outer layer of the skin has distinct electrical properties. When skin is dry it conducts electricity very poorly. As it becomes more hydrated increasing conductivity results. Consequently, changes in skin impedance (related to conductivity) can be used to assess changes in skin hydration. The unit can be calibrated according to instrument instructions for each testing day. A notation of temperature and relative humidity can also be made. Subjects can be evaluated as follows: prior to measurement they can equilibrate in a room with defined humidity (e.g., 30-50%) and temperature (e.g., 68-72° C.). Three separate impedance readings can be taken on each side of the face, recorded, and averaged. The T5 setting can be used on the impedance meter which averages the impedance values of every five seconds application to the face. Changes can be reported with statistical variance and significance.

Skin Clarity and Reduction in Freckles and Age Spots Assay:

Skin clarity and the reduction in freckles and age spots can be evaluated using a Minolta Chromometer. Changes in skin color can be assessed to determine irritation potential due to product treatment using the a* values of the Minolta Chroma Meter. The a* value measures changes in skin color in the red region. This is used to determine whether a composition is inducing irritation. The measurements can be made on each side of the face and averaged, as left and right facial values. Skin clarity can also be measured using the Minolta Meter. The measurement is a combination of the a*, b, and L values of the Minolta Meter and is related to skin brightness, and correlates well with skin smoothness and hydration. Skin reading is taken as above. In one non-limiting) aspect, skin clarity can be described as L/C where C is chroma and is defined as $(a^2+b^2)^{1/2}$.

Skin Dryness, Surface Fine Lines, Skin Smoothness, and Skin Tone Assay:

Skin dryness, surface fine lines, skin smoothness, and skin tone can be evaluated with clinical grading techniques. For example, clinical grading of skin dryness can be determined by a five point standard Kligman Scale: (0) skin is soft and moist; (1) skin appears normal with no visible dryness; (2) skin feels slightly dry to the touch with no visible flaking; (3) skin feels dry, tough, and has a whitish appearance with some scaling; and (4) skin feels very dry, rough, and has a whitish appearance with scaling. Evaluations can be made independently by two clinicians and averaged.

Clinical Grading of Skin Tone Assay:

Clinical grading of skin tone can be performed via a ten point analog numerical scale: (10) even skin of uniform, pinkish brown color. No dark, erythremic, or scaly patches upon examination with a hand held magnifying lens. Microtexture of the skin very uniform upon touch; (7) even skin tone observed without magnification. No scaly areas, but slight discolorations either due to pigmentation or erythema. No discolorations more than 1 cm in diameter; (4) both skin discoloration and uneven texture easily noticeable. Slight scaliness. Skin rough to the touch in some areas; and (1) uneven skin coloration and texture. Numerous areas of scaliness and discoloration, either hypopigmented, erythremic or dark spots. Large areas of uneven color more than 1 cm in diameter. Evaluations were made independently by two clinicians and averaged.

Clinical Grading of Skin Smoothness Assay:

Clinical grading of skin smoothness can be analyzed via a ten point analog numerical scale: (10) smooth, skin is moist and glistening, no resistance upon dragging finger across surface; (7) somewhat smooth, slight resistance; (4) rough, visibly altered, friction upon rubbing; and (1) rough, flaky, uneven surface. Evaluations were made independently by two clinicians and averaged.

Skin Smoothness and Wrinkle Reduction Assay with Methods Disclosed in Packman et al. (1978):

Skin smoothness and wrinkle reduction can also be assessed visually by using the methods disclosed in Packman et al. (1978). For example, at each subject visit, the depth, shallowness and the total number of superficial facial lines (SFLs) of each subject can be carefully scored and recorded. A numerical score was obtained by multiplying a number factor times a depth/width/length factor. Scores are obtained for the eye area and mouth area (left and right sides) and added together as the total wrinkle score.

Skin Firmness Assay with a Hargens Ballistometer:

Skin firmness can be measured using a Hargens ballistometer, a device that evaluates the elasticity and firmness of the skin by dropping a small body onto the skin and recording its first two rebound peaks. The ballistometry is a small lightweight probe with a relatively blunt tip (4 square mm-contact area) was used. The probe penetrates slightly into the skin and results in measurements that are dependent upon the properties of the outer layers of the skin, including the stratum corneum and outer epidermis and some of the dermal layers.

Skin Softness/Suppleness Assay with a Gas Bearing Electrodynamometer:

Skin softness/suppleness can be evaluated using the Gas Bearing Electrodynamometer, an instrument that measures the stress/strain properties of the skin. The viscoelastic properties of skin correlate with skin moisturization. Measurements can be obtained on the predetermined site on the cheek area by attaching the probe to the skin surface with double-stick tape. A force of approximately 3.5 gm can be applied parallel to the skin surface and the skin displacement is accurately measured. Skin suppleness can then be calculated and is expressed as DSR (Dynamic Spring Rate in gm/mm).

Appearance of Lines and Wrinkles Assay with Replicas:

The appearance of lines and wrinkles on the skin can be evaluated using replicas, which is the impression of the skin's surface. Silicone rubber like material can be used. The replica can be analyzed by image analysis. Changes in the visibility of lines and wrinkles can be objectively quantified via the taking of silicon replicas form the subjects' face and analyzing the replicas image using a computer image analysis system. Replicas can be taken from the eye area and the neck area, and photographed with a digital camera using a low angle incidence lighting. The digital images can be analyzed with an image processing program and the area of the replicas covered by wrinkles or fine lines was determined.

Surface Contour of the Skin Assay with a Profilometer/Stylus Method:

The surface contour of the skin can be measured by using the profilometer/Stylus method. This includes either shining a light or dragging a stylus across the replica surface. The vertical displacement of the stylus can be fed into a computer via a distance transducer, and after scanning a fixed length of replica a cross-sectional analysis of skin profile can be generated as a two-dimensional curve. This scan can be repeated any number of times along a fix axis to generate a simulated 3-D picture of the skin. Ten random sections of the replicas using the stylus technique can be obtained and combined to generate average values. The values of interest include Ra which is the arithmetic mean of all roughness (height) values computed by integrating the profile height relative to the mean profile height. Rt which is the maximum vertical distance between the highest peak and lowest trough, and Rz which is the mean peak amplitude minus the mean peak height. Values are given as a calibrated value in mm. Equipment should be standardized prior to each use by scanning metal standards of know values. Ra Value can be computed by the following equation: $R_a$=Standardize roughness; $l_m$=the traverse (scan) length; and y=the absolute value of the location of the profile relative to the mean profile height (x-axis).

MELANODERM™ Assay:

In other non-limiting aspects, the efficacy of the compositions of the present invention can be evaluated by using a skin analog, such as, for example, MELANODERM™. Melanocytes, one of the cells in the skin analog, stain positively when exposed to L-dihydroxyphenyl alanine (L-DOPA), a precursor of melanin. The skin analog, MELANODERM™, can be treated with a variety of bases containing the compositions and whitening agents of the present invention or with the base alone as a control. Alternatively, an untreated sample of the skin analog can be used as a control.

ORAC Assay:

Oxygen Radical Absorption (or Absorbance) Capacity (ORAC) of the aromatic skin-active ingredients and compositions can also be assayed by measuring the antioxidant activity of such ingredients or compositions. This assay can quantify the degree and length of time it takes to inhibit the action of an oxidizing agent such as oxygen radicals that are known to cause damage cells (e.g., skin cells). The ORAC value of the aromatic skin-active ingredients and compositions can be determined by methods known to those of ordinary skill in the art (see U.S. Publication Nos. 2004/0109905 and 2005/0163880; Cao et al. (1993)), all of which are incorporated by reference). In summary, the assay described in Cao et al. (1993) measures the ability of antioxidant compounds in test materials to inhibit the decline of B-phycoerythrm (B-PE) fluorescence that is induced by a peroxyl radical generator, AAPH.

Matrix Metalloproteinase Enzyme Activity (MMP3; MMP9) Assay:

An in vitro matrix metalloprotease (MMP) inhibition assay. MMPs are extracellular proteases that play a role in many normal and disease states by virtue of their broad substrate specificity. MMP3 substrates include collagens, fibronectins, and laminin; while MMP9 substrates include collagen VII, fibronectins and laminin. Using Colorimetric Drug Discovery kits from BioMol International for MMP3 (AK-400) and MMP-9 (AK-410), this assay is designed to measure protease activity of MMPs using a thiopeptide as a chromogenic substrate (Ac-PLG-[2-mercapto-4-methyl-pentanoyl]-LG-OC2H5)5,6. The MMP cleavage site peptide bond is replaced by a thioester bond in the thiopeptide. Hydrolysis of this bond by an MMP produces a sulfhydryl group, which reacts with DTNB [5,5'-dithiobis(2-nitrobenzoic acid), Ellman's reagent] to form 2-nitro-5-thiobenzoic acid, which can be detected by its absorbance at 412 nm ($\varepsilon$=13,600 M−1 cm−1 at pH 6.0 and above 7).

B16 Pigmentation Assay:

Melanogenesis is the process by which melanocytes produce melanin, a naturally produced pigment that imparts color to skin, hair, and eyes. Inhibiting melanogenesis is beneficial to prevent skin darkening and lighten dark spots associated with aging. This bioassay utilizes B16-F1 melanocytes (ATCC), an immortalized mouse melanoma cell line, to analyze the effect of compounds on melanogenesis. The endpoint of this assay is a spectrophotometric measurement of melanin production and cellular viability. B16-F1 melanocytes, can be cultivated in standard DMEM growth medium with 10% fetal bovine serum (Mediatech) at 37° C. in 10% $CO_2$ and then treated with any one of the active ingredients, combination of ingredients, or compositions having said combinations disclosed in the specification for 6 days. Following incubation, melanin secretion was measured by absorbance at 405 nm and cellular viability was quantified.

Collagen Stimulation Assay:

Collagen is an extracellular matrix protein critical for skin structure. Increased synthesis of collagen helps improve skin firmness and elasticity. This bioassay can be used to examine the effect of any one of the active ingredients, combination of ingredients, or compositions having said combinations disclosed in the specification on the production of procollagen peptide (a precursor to collagen) by human epidermal fibroblasts. The endpoint of this assay is a spectrophotometric measurement that reflects the presence of procollagen peptide and cellular viability. The assay employs the quantitative sandwich enzyme immunoassay technique whereby a monoclonal antibody specific for procollagen peptide has been pre-coated onto a microplate. Standards and samples can be pipetted into the wells and any procollagen peptide present is bound by the immobilized antibody. After washing away any unbound substances, an enzyme-linked polyclonal antibody specific for procollagen peptide can be added to the wells. Following a wash to remove any unbound antibody-enzyme reagent, a substrate solution can be added to the wells and color develops in proportion to the amount of procollagen peptide bound in the initial step using a microplate reader for detection at 450 nm. The color development can be stopped and the intensity of the color can be measured. Subconfluent normal human adult epidermal fibroblasts (Cascade Biologics) cultivated in standard DMEM growth medium with 10% fetal bovine serum (Mediatech) at 37° C. in 10% $CO_2$, can be treated with each of the combination of ingredients or compositions having said combinations disclosed in the specification for 3 days. Following incubation, cell culture medium can be collected and the amount of procollagen peptide secretion quantified using a sandwich enzyme linked immuno-sorbant assay (ELISA) from Takara (#MK101).

Tumor Necrosis Factor Alpha (TNF-α) Assay:

The prototype ligand of the TNF superfamily, TNF-α, is a pleiotropic cytokine that plays a central role in inflammation. Increase in its expression is associated with an up regulation in pro-inflammatory activity. This bioassay can be used to analyze the effect of any one of the active ingredients, combination of ingredients, or compositions having said combinations disclosed in the specification on the production of TNF-α by human epidermal keratinocytes. The endpoint of this assay can be a spectrophotometric measurement that reflects the presence of TNF-α and cellular viability. The assay employs the quantitative sandwich enzyme immunoassay technique whereby a monoclonal antibody specific for TNF-α has been pre-coated onto a microplate. Standards and samples can be pipetted into the wells and any TNF-α present is bound by the immobilized antibody. After washing away any unbound substances, an enzyme-linked polyclonal antibody specific for TNF-α can be added to the wells. Following a wash to remove any unbound antibody-enzyme reagent, a substrate solution can be added to the wells and color develops in proportion to the amount of TNF-α bound in the initial step using a microplate reader for detection at 450 nm. The color development can be stopped and the intensity of the color can be measured. Subconfluent normal human adult keratinocytes (Cascade Biologics) cultivated in EpiLife standard growth medium (Cascade Biologics) at 37° C. in 5% $CO_2$, can be treated with phorbol 12-myristate 13-acetate (PMA, 10 ng/ml, Sigma Chemical, #P1585-1MG) and any one of the active ingredients, combination of ingredients, or compositions having said combinations disclosed in the specification for 6 hours. PMA has been shown to cause a dramatic increase in TNF-α secretion which peaks at 6 hours after treatment. Following incubation, cell culture medium can be collected and the amount of TNF-α secretion quantified using a sandwich enzyme linked immuno-sorbant assay (ELISA) from R&D Systems (#DTA00C).

Antioxidant (AO) Assay:

An in vitro bioassay that measures the total anti-oxidant capacity of any one of the ingredients, combination of ingredients, or compositions having said combinations disclosed in the specification. The assay relies on the ability of antioxidants in the sample to inhibit the oxidation of ABTS® (2,2'-azino-di-[3-ethylbenzthiazoline sulphonate]) to ABTS®+ by metmyoglobin. The antioxidant system of living organisms includes enzymes such as superoxide dismutase, catalase, and glutathione peroxidase; macromolecules such as albumin, ceruloplasmin, and ferritin; and an array of small molecules, including ascorbic acid, α-tocopherol, β-carotene, reduced glutathione, uric acid, and bilirubin. The sum of endogenous and food-derived antioxidants represents the total antioxidant activity of the extracellular fluid. Cooperation of all the different antioxidants provides greater protection against attack by reactive oxygen or nitrogen radicals, than any single compound alone. Thus, the overall antioxidant capacity may give more relevant biological information compared to that obtained by the measurement of individual components, as it considers the cumulative effect of all antioxidants present in plasma and body fluids. The capacity of the antioxidants in the sample to prevent ABTS oxidation is compared with that of Trolox, a water-soluble tocopherol analogue, and is quantified as molar Trolox equivalents. Anti-Oxidant capacity kit #709001 from Cayman Chemical (Ann Arbor, Mich. USA) can be used as an in vitro bioassay to measure the total anti-oxidant capacity of each of any one of the active ingredients, combination of ingredients, or compositions having said combinations disclosed in the specification. The protocol can be followed according to manufacturer recommendations. The assay relied on antioxidants in the sample to inhibit the oxidation of ABTS® (2,2'-azino-di-[3-ethyl-benzthiazoline sulphonate]) to ABTS®+ by metmyoglobin. The capacity of the antioxidants in the sample to prevent ABTS oxidation can be compared with that Trolox, a water-soluble tocopherol analogue, and was quantified as a molar Trolox equivalent.

Mushroom Tyrosinase Activity Assay:

In mammalian cells, tyrosinase catalyzes two steps in the multi-step biosynthesis of melanin pigments from tyrosine (and from the polymerization of dopachrome). Tyrosinase is localized in melanocytes and produces melanin (aromatic quinone compounds) that imparts color to skin, hair, and eyes. Purified mushroom tyrosinase (Sigma) can be incubated with its substrate L-Dopa (Fisher) in the presence or absence of each of the active ingredients, any one of the combination of ingredients, or compositions having said combinations disclosed in the specification. Pigment formation can be evaluated by colorimetric plate reading at 490 nm. The percent inhibition of mushroom tyrosinase activity can be calculated compared to non-treated controls to determine the ability of test ingredients or combinations thereof to inhibit the activity of purified enzyme. Test ingredient inhibition can be compared with that of kojic acid (Sigma).

Cyclooxygenase (COX) Assay:

An in vitro cyclooxygenase-1 and -2 (COX-1, -2) inhibition assay. COX is a bifunctional enzyme exhibiting both cyclooxygenase and peroxidase activities. The cyclooxygenase activity converts arachidonic acid to a hydroperoxy endoperoxide (Prostaglandin G2; PGG2) and the peroxidase component reduces the endoperoxide (Prostaglandin H2; PGH2) to the corresponding alcohol, the precursor of prostaglandins, thromboxanes, and prostacyclins. This COX Inhibitor screening assay measures the peroxidase component of cyclooxygenases. The peroxidase activity is assayed colorimetrically by monitoring the appearance of oxidized N,N,N',N'-tetramethyl-p-phenylenediamine (TMPD). This inhibitor screening assay includes both COX-1 and COX-2 enzymes in order to screen isozyme-specific inhibitors. The Colormetric COX (ovine) Inhibitor screening assay (#760111, Cayman Chemical) can be used to analyze the effects of each of the active ingredients, any one of the combination of ingredients, or compositions having said combinations disclosed in the specification on the activity of purified cyclooxygnase enzyme (COX-1 or COX-2). According to manufacturer instructions, purified enzyme, heme and test ingredients can be mixed in assay buffer and incubated with shaking for 15 min at room temperature. Following incubation, arachidonic acid and colorimetric substrate can be added to initiate the reaction. Color progression can be evaluated by colorimetric plate reading at 590 nm. The percent inhibition of COX-1 or COX-2 activity can be calculated compared to non-treated controls to determine the ability of test ingredients to inhibit the activity of purified enzyme.

Lipoxygenase (LO) Assay:

An in vitro lipoxygenase (LO) inhibition assay. LOs are non-heme iron-containing dioxygenases that catalyze the addition of molecular oxygen to fatty acids. Linoleate and arachidonate are the main substrates for LOs in plants and animals. Arachadonic acid may then be converted to hydroxyeicosotrienenoic (HETE) acid derivatives, that are subsequently converted to leukotirenes, potent inflammatory mediators. This assay provides an accurate and convenient method for screening lipoxygenase inhibitors by measuring the hydroperoxides generated from the incubation of a lipoxygenase (5-, 12-, or 15-LO) with arachidonic acid. The Colorimetric LO Inhibitor screening kit (#760700, Cayman Chemical) can be used to determine the ability of each of the active ingredients, any one of the combination of ingredients, or compositions having said combinations disclosed in the specification to inhibit enzyme activity. Purified 15-lipoxygenase and test ingredients can be mixed in assay buffer and incubated with shaking for 10 min at room temperature. Following incubation, arachidonic acid can be added to initiate the reaction and mixtures incubated for an additional 10 min at room temperature. Colorimetric substrate can be added to terminate catalysis and color progression was evaluated by fluorescence plate reading at 490 nm. The percent inhibition of lipoxyganse activity can be calculated compared to non-treated controls to determine the ability of each of the active ingredients, any one of the combination of ingredients, or compositions having said combinations disclosed in the specification to inhibit the activity of purified enzyme.

Elastase Assay:

EnzChek® Elastase Assay (Kit# E-12056) from Molecular Probes (Eugene, Oreg. USA) can be used as an in vitro enzyme inhibition assay for measuring inhibition of elastase activity for each of the active ingredients, any one of the combination of ingredients, or compositions having said combinations disclosed in the specification. The EnzChek kit contains soluble bovine neck ligament elastin that can be labeled with dye such that the conjugate's fluorescence can be quenched. The non-fluorescent substrate can be digested by elastase or other proteases to yield highly fluorescent fragments. The resulting increase in fluorescence can be monitored with a fluorescence microplate reader. Digestion products from the elastin substrate have absorption maxima at ~505 nm and fluorescence emission maxima at ~515 nm. The peptide, chloromethyl ketone, can be used as a selective, collective inhibitor of elastase when utilizing the EnzChek Elastase Assay Kit for screening for elastase inhibitors.

Oil Control Assay:

An assay to measure reduction of sebum secretion from sebaceous glands and/or reduction of sebum production from sebaceous glands can be assayed by using standard techniques known to those having ordinary skill in the art. In one instance, the forehead can be used. Each of the active ingredients, any one of the combination of ingredients, or compositions having said combinations disclosed in the specification can be applied to one portion of the forehead once or twice daily for a set period of days (e.g., 1, 2, 3, 4, 5, 6, 7, 8, 9, 10, 11, 12, 13, 14, or more days), while another portion of the forehead is not treated with the composition. After the set period of days expires, then sebum secretion can be assayed by application of fine blotting paper to the treated and untreated forehead skin. This is done by first removing any sebum from the treated and untreated areas with moist and dry cloths. Blotting paper can then be applied to the treated and untreated areas of the forehead, and an elastic band can be placed around the forehead to gently press the blotting paper onto the skin. After 2 hours the blotting papers can be removed, allowed to dry and then transilluminated. Darker blotting paper correlates with more sebum secretion (or lighter blotting paper correlates with reduced sebum secretion.

All of the skin-active ingredients, compositions, or methods disclosed and claimed in this specification can be made and executed without undue experimentation in light of the present disclosure. While the skin-active ingredients, compositions, or methods of this invention have been described in terms of particular embodiments, it will be apparent to those of skill in the art that variations may be applied to the skin-active ingredients, compositions, or methods and in the steps or in the sequence of steps of the method described herein without departing from the concept, spirit and scope of the invention.

REFERENCES

The following references, to the extent that they provide exemplary procedural or other details supplementary to those set forth herein, are specifically incorporated herein by reference. Cao et al. 1993.

International Cosmetic Ingredient Dictionary and Handbook, 12$^{th}$ Edition, 2008 ("CTFA"), Volume 2 page 2399

International Cosmetic Ingredient Dictionary and Handbook, 12$^{th}$ Edition, 2008 ("CTFA"), Volume 1 page 198, page 655

International Cosmetic Ingredient Dictionary and Handbook, 4$^{th}$ Edition, 1991 ("CTFA"), pp. 12 and 80

The invention claimed is:

1. A method for reducing the appearance of a skin pore in skin of a subject in need thereof, the method comprising topically applying to the skin pore a composition comprising effective amount of:
   *Albizia julibrissin* bark extract;
   *Evodia rutaecarpa* fruit extract;
   hydrolyzed soy flour; and
   sea whip extract,
   wherein topical application of the composition reduces the size of the skin pore.

2. The method of claim 1, wherein the *Albizia julibrissin* bark extract is a glycerin extract of *Albizia julibrissin* bark or aqueous glycerin extract of *Albizia julibrissin* bark.

3. The method of claim 1, wherein the *Evodia rutaecarpa* fruit extract is a propanediol extract of *Evodia rutaecarpa* fruit.

4. The method of claim 1, wherein the hydrolyzed soy flour comprises glycoproteins and polysaccharides from soybean cell walls.

5. The method of claim 1, wherein the sea whip extract is an ethanol extract comprising pseudopterosins from *Pseudopterogorgia elisabethae*.

6. The method of claim 1, wherein:
   the *Albizia julibrissin* bark extract is a glycerin extract of *Albizia julibrissin* bark or aqueous glycerin extract of *Albizia julibrissin* bark,
   the *Evodia rutaecarpa* fruit extract is a propanediol extract of *Evodia rutaecarpa* fruit;
   the hydrolyzed soy flour comprises glycoproteins and polysaccharides from soybean cell walls; and
   the sea whip extract is an ethanol extract comprising pseudopterosins from *Pseudopterogorgia elisabethae*.

7. The method of claim 1, wherein the composition comprises:
   0.1 to 1% by weight of *Albizia julibrissin* bark extract;
   0.01 to 0.5% by weight of *Evodia rutaecarpa* fruit extract;
   0.01 to 0.5% by weight of hydrolyzed soy flour; and
   0.001 to 0.05% by weight of sea whip extract.

8. The method of claim 1, wherein the composition further comprises:
   glycerin;
   cyclopentasiloxane;
   polysilicone-11;
   pentaerythrityl tetraethylhexanoate;
   dipropylene glycol;
   methyl methacrylate crosspolymer;
   betaine; and
   bis-PEG/PPG-16/PPG-16/16 PEG/16 dimethicone.

9. The method of claim 1, wherein the composition comprises:
   3 to 10% by weight of glycerin;
   2 to 8% by weight of cyclopentasiloxane;
   1 to 6% by weight of polysilicone-11;
   1 to 6% by weight of pentaerythrityl tetraethylhexanoate;
   1 to 6% by weight of dipropylene glycol;
   1 to 6% by weight of methyl methacrylate crosspolymer;
   0.5 to 4% by weight of betaine; and
   0.5 to 4% by weight of bis-PEG/PPG-16/PPG-16/16 PEG/16 dimethicone.

10. The method of claim 1, wherein the composition is an emulsion, cream, lotion, solution, anhydrous base, or gel.

11. The method of claim 10, wherein the composition is a solution.

12. The method of claim 1, further comprising one or more additional ingredients selected from one or more preservatives, emulsifiers, conditioning agents, thickening agents, fragrances, moisturizing agents, chelating agents, structuring agents, and colorants.

13. The method of claim 1, wherein the skin is cleansed prior to application of the composition.

14. The method of claim 1 wherein the composition is applied daily.

* * * * *